United States Patent [19]

Saito et al.

[11] Patent Number: 4,682,897

[45] Date of Patent: Jul. 28, 1987

[54] LIGHT SCATTERING MEASURING APPARATUS

[75] Inventors: Kenji Saito, Tokyo; Ken Eguchi, Yokohama; Haruki Kawada, Kawasaki; Yoshinori Tomida, Yokohama; Yukuo Nishimura, Sagamihara; Takashi Nakagiri, Tokyo, all of Japan

[73] Assignee: Canon Kabushiki Kaisha, Tokyo, Japan

[21] Appl. No.: 804,108

[22] Filed: Dec. 3, 1985

[30] Foreign Application Priority Data

| Dec. 10, 1984 | [JP] | Japan | 59-259072 |
|---|---|---|---|
| Dec. 10, 1984 | [JP] | Japan | 59-259073 |
| Dec. 10, 1984 | [JP] | Japan | 59-259074 |
| Dec. 10, 1984 | [JP] | Japan | 59-259075 |
| Dec. 10, 1984 | [JP] | Japan | 59-259076 |

[51] Int. Cl.$^4$ .................. G01N 21/41; G01N 25/72
[52] U.S. Cl. ......................... 374/45; 250/215; 356/339; 374/7; 374/117; 374/142
[58] Field of Search .............. 374/117; 73/643; 250/215, 250; 356/337, 339

[56] References Cited

U.S. PATENT DOCUMENTS

| 3,978,713 | 9/1976 | Penny | 73/643 X |
|---|---|---|---|
| 4,048,500 | 9/1977 | Moore | 250/350 |
| 4,137,991 | 2/1979 | Melcher et al. | 73/643 X |
| 4,242,194 | 12/1980 | Steiner et al. | 356/337 X |
| 4,243,327 | 1/1981 | Frosch et al. | 374/45 X |
| 4,276,780 | 7/1981 | Patel et al. | 73/643 |
| 4,329,053 | 5/1982 | Fletcher et al. | 356/338 X |
| 4,468,136 | 8/1984 | Murphy et al. | 374/45 |
| 4,521,118 | 6/1985 | Rosencwaig | 374/5 |
| 4,579,463 | 4/1986 | Rosencwaig | 374/4 X |

FOREIGN PATENT DOCUMENTS

| 56-122936 | 9/1981 | Japan. | |
|---|---|---|---|
| 60-6854 | 1/1985 | Japan | 356/337 |

OTHER PUBLICATIONS

IBM Technical Disclosure Bulletin, "Detection of Pin Holes in Their Layers By Ultrasonic Cavitation", vol. 22, No. 2, 1979, pp. 615–616.

Primary Examiner—Daniel M. Yasich
Attorney, Agent, or Firm—Fitzpatrick, Cella, Harper & Scinto

[57] ABSTRACT

A light scattering measuring apparatus utilizes light scattering to analyze physical properties of the surface and interior of an object, and particularly converts the scattered light therefrom into molecular vibrational energy or heat energy and measures the same. The light scattering measuring apparatus is provided with light applying means for applying an intermittent light to an object to be examined, a medium for absorbing scattered light intermittently emitted from the surface of the object by the applied light in accordance with the physical properties of the object to be examined and converting the scatterd light into molecular vibrational energy or heat energy, a detecting device for detecting the information regarding the energy produced by the medium, and a measuring device for measuring the molecular vibrational energy or the heat energy on the basis of a signal produced by the detecting device.

17 Claims, 23 Drawing Figures

LIGHT SCATTERING MEASURING APPARATUS

BACKGROUND OF THE INVENTION

1. Field of the Invention

This invention relates to an apparatus utilizing light scattering to analyze physical properties of the surface and interior of an object, and in particular to an apparatus for converting the scattered light therefrom into molecular vibrational energy or heat energy and measuring the same.

2. Description of the Related Art

Figure 3:
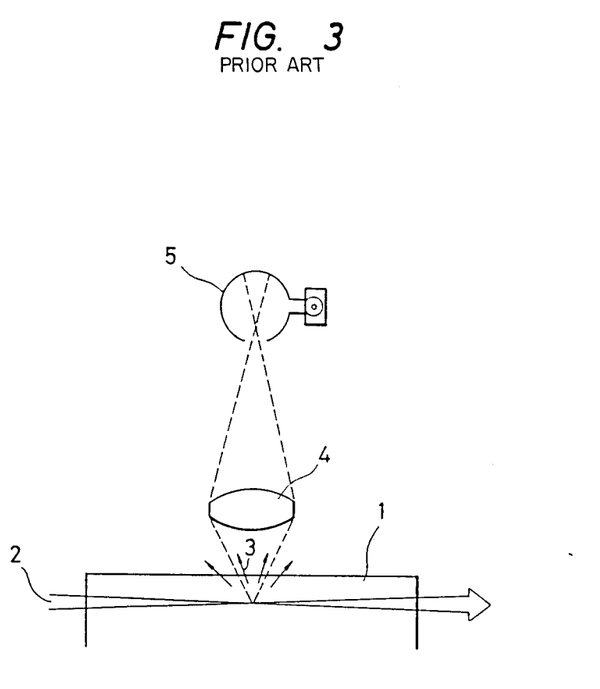
FIG. 3 shows the construction of the prior art.

Heretofore, in an apparatus utilizing light scattering to analyze the physical properties of the surface and interior of an object, as shown in FIG. 3 of the accompanying drawings, a light 2 has been applied to an object 1 to be examined, and scattered light 3 has been passed through a lens 4 having a great angular aperture and has been further directed to the photosensitive surface of a photodetector (such as a photomultiplier or a p-i-n photodiode) through an integration ball 5 to decrease the influence of a luminous intensity distribution. In this case, however, if the angle of scattering is greater than the angular aperture, the outside scattered component cannot enter the lens and thus, measurement has been impossible. In order to detect the outside scattered component, a technique of placing a diffusing surface of the transmission type near the object to be examined and placing a photodetector behind it has been devised, but this technique has suffered from problems, for example, in the characteristic of the diffusing plate and the manner in which the photodetector is installed, and therefore measurement at high accuracy and high sensitivity has been difficult.

SUMMARY OF THE INVENTION

In view of the above-noted point, the present invention intends to solve the problems encountered in effecting measurement at high accuracy and high sensitivity, including the measurement of the light scattering component of a great angle of scattering which it has been difficult to measure by a light scattering measuring apparatus of the conventional type.

That is, the present invention is a light scattering measuring apparatus provided with light applying means for applying an intermittent light to an object to be examined, a photosensitive medium for absorbing scattered light intermittently emitted from the surface of said object, by the applied light in accordance with physical properties of said object to be examined and converting the scattered light into molecular vibrational energy, energy signal detecting means for detecting an intermittent energy signal produced in said medium, and molecular vibration measuring means for frequency-synchronously detecting the energy signal by a reference signal from said light applying means.

Furthermore, the present invention is a light scattering measuring means provided with light applying means for applying an intermittent light to an object to be examined, a light-heat converting medium for absorbing scattered light intermittently emitted from the surface of said object by the applied light in accordance with physical properties of said object to be examined and converting the scattered light into heat energy, elastic wave detecting means for detecting an elastic wave created by the heat energy as an electrical signal by piezoelectric conversion, and heat variation measuring means for measuring the amount of said heat energy from the electrical signal.

DESCRIPTION OF THE PREFERRED EMBODIMENTS

Figure 1:
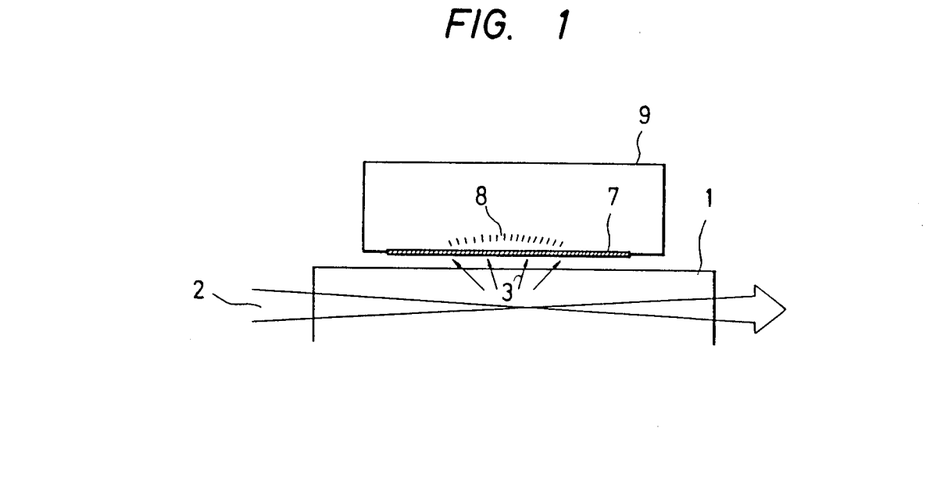
FIG. 1 shows the construction of the present invention.

FIG. 1 shows the basic construction of a light scattering measuring apparatus according to the present invention. In FIG. 1, when an intermittent light 2 is applied to an object 1 to be examined, the scattered light 3 by the light in the object to be examined is intermittently emitted from the surface of the object to be examined at various angles of emergence. A photosensitive medium 7 is formed of a light absorbing substance, and the applied light energy is absorbed and becomes an intermittent molecular vibrational energy signal 8, which is directed to energy signal detecting means 9. For any angle of incidence, the light signal is converted into a molecular vibrational energy signal and therefore, by suitably setting the size and position of the photosensitive medium 7, the light signal can be easily detected even in a case where the angle of scattering is great.

A conventional light source and a chopper are used as intermittent light applying means, and a light absorbing substance having a great absorption characteristic for the wavelength of the scattered light to be measured and having a good thermal conductivity is preferred as the material of the photosensitive medium, and if use is made of carbon and a mixture consisting chiefly of carbon, a wide range of wavelength area can be covered. By premeasuring the absorption characteristics for each wavelength of the light absorbing substance, correction of the output signal can be effected and the sensitivity irregularity for each wavelength can be corrected. As regards the surface configuration of the light absorbing substance, concave-convexity somewhat greater than the wavelength of the scattered light is provided to thereby improve the complete diffusivity and thus, not only the influence of the angle of scattering can be eliminated, but also the absorption efficiency can be enhanced. Energy signal detecting means may be one corresponding to the molecular vibrational energy signal produced in the medium. For example, a microphone or the like is used for sound wave and a thermocouple is used for heat. A lock-in amplifier is used as molecular vibration measuring means.

The object to be examined is not restricted to a solid, but may also be liquid, and by applying an irradiating light to the surface of liquid, it is also applicable to the development situation of monomolecular film on the surface of liquid, i.e., so-called LB film (Langmuir-Blodgett film), or to the evaluation of the fine particles in the liquid near the adsorped molecule interface.

In FIG. 1, it has been stated that the energy signal detecting means may be one corresponding to the molecular vibrational energy signal produced in the medium, but the form of the molecular vibrational energy signal is changed as follows by an opto-acoustic effect.

Figure 2:
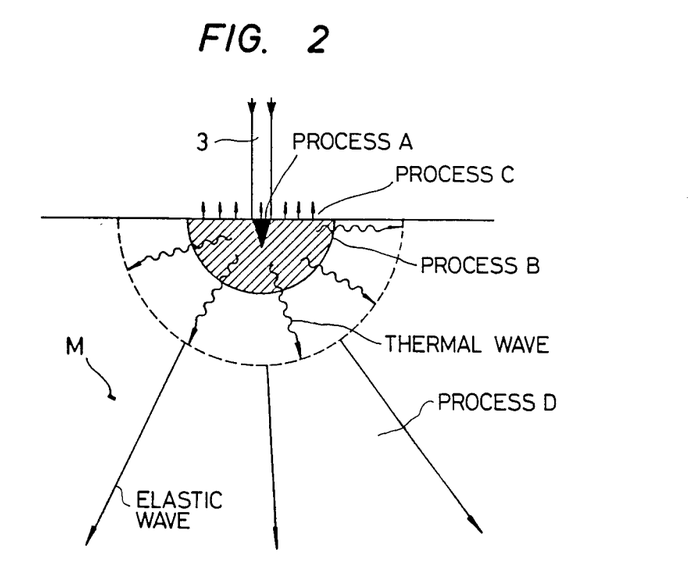
FIG. 2 illustrates the principle of the opto-acoustic effect.

FIG. 2 illustrates the basic principle of the opto-acoustic effect. In FIG. 2, the opto-acoustic effect comprises four processes and there is shown a state in which energy is propagated through the substance by the substance absorbing light. The process A shows the process in which the intermittently modulated incident light beam 3 impinges on and is absorbed by the absorbing substance. The process B shows the process in which this energy is made into intermittent heat by a non-radiation relaxation process and is propagated as a heat wave through the substance. The process C shows the case where the heat wave having reached the surface of the substance intermittently heats the gas which is in contact with the substance and produces a sound wave, and the process D shows the case where the heat wave propagated through the substance is converted into an elastic wave and is propagated through a sample M. The present invention intends to select a desired form of molecular vibrational energy from the stage of one of the above-described processes and detect a required signal by energy signal detecting means, and can detect such a signal at high sensitivity by the utilization of opto-acoustic means which is a phenomenon exhibiting an acoustic reaction, a surface temperature distribution, etc.

As the scattering which is the object of the analysis by the present invention, there are so-called elastic scattering in which scattered light is not accompanied by wavelength shift and non-elastic scattering such as Raman scattering or Brillouin scattering in which scattered light is accompanied by wavelength shift. As the analysis using both of elastic scattered light and non-elastic scattered light, mention may be made, for example, of a method in which a light stopped down to a predetermined diameter is applied to a transparent crystal member and all the scattered light therefrom is used as an information source. The scattered light in this case includes lights of all wavelength components, and this method is simple and convenient as a method of finding the fluctuation of the refractive index in the surface and interior of the object to be examined and the presence of fine particles.

As regards the analysis by the non-elastic scattering, if Raman scattering (or laser Raman spectrum) created by the utilization of a monochromatic light as represented, for example, by laser light, is analyzed, it will be possible to obtain the molecular structural information in a minute portion of the interior of the object to be examined. For example, by using the analysis of phase transition by the variation in the frequency of scattered light attributable to a variation in the vibration of grating, particularly, by changing the temperature of the object to be examined and using the analyzing method of the present invention, various types of information can be obtained with respect to a localized variation in phase transition.

Furthermore, in the analysis using Brillouin scattering, scattered light accompanied by the wavelength shift caused by the interaction between the phonon in the object to be examined and the applied light is used as the information source and therefore, if this is spectroscopically analyzed, it will be effective, for example, for the analysis of the phase transition of a crystal sample and the analysis of the glass transition of a high molecular substance.

The present invention will hereinafter be described in detail with respect to some embodiments thereof shown in the drawings.

Figure 4:
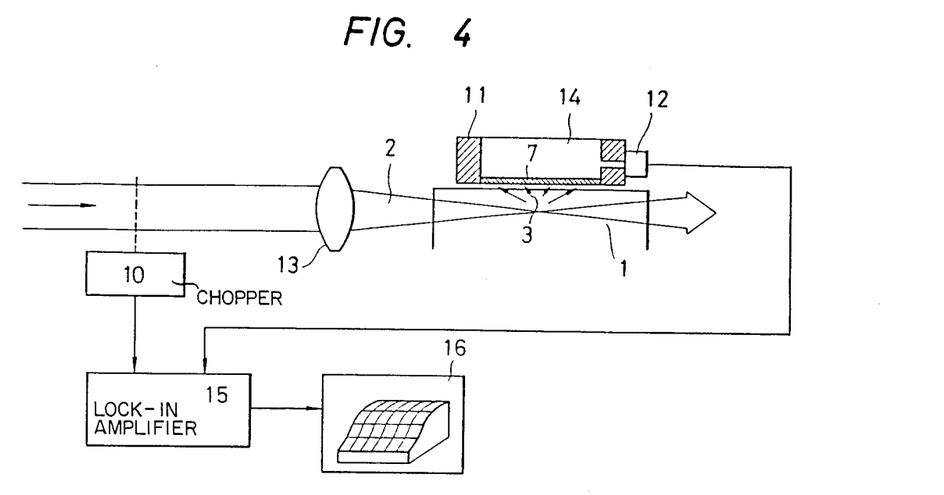
FIGS. 4, 7, 9, 12 and 15 show the constructions of embodiments of the present invention.

FIG. 4 shows an example of the construction of a light scattering measuring apparatus in which the present invention is embodied, and in this embodiment, the energy signal is a sound wave produced by said process C and the energy signal detecting means is a microphone. In FIG. 4, a conventional light source and a chopper 10 are used as light applying means which constitutes the light scattering measuring apparatus, and the photosensitive medium is the photosensitive surface 7 of a microphone cell 11 and the energy signal detecting means is a microphone 12. An applied light beam 2 interrupted by the chopper 10 is directed to an object 1 to be examined by a lens 13, and the scattered light 3 therefrom is absorbed by the photosensitive surface 7 of the microphone cell 11 and intermittently heats the gas 14 in the hermetically sealed microphone cell 11 to thereby produce a sound wave. This sound wave is detected by the microphone 12 attached to the microphone cell 11, and the signal from the microphone 12 is supplied to a lock-in amplifier 15 which is molecular vibration measuring means and is frequency-synchronously detected on the basis of the reference signal from the chopper 10 which interrupts the measuring light beam 2, and the result is put out to a recorder 16. It is theoretically confirmed that the intensity of the thus detected opto-acoustic signal is proportional to the intensity of the scattered light applied to a light absorbing substance. Accordingly, the intensity of the scattered light can be quantitatively measured.

The measurement will be more stabilized if the intensity of the incident light is monitored and the fluctuation of the intensity of the applied light is eliminated. Also, the light scattering distribution can also be measured by moving the position in which light is applied to the object to be examined. The application of light to the object to be examined may be not only in the direction shown in FIG. 4, but also in any direction.

Figure 5:
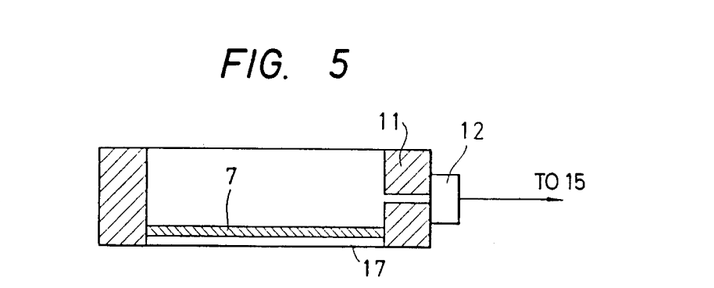
FIGS. 5, 6, 8, 10, 11, 13, 16, 17 and 19–23 are longitudinal cross-sectional views of energy signal detecting means in the respective embodiments.
Figure 6:
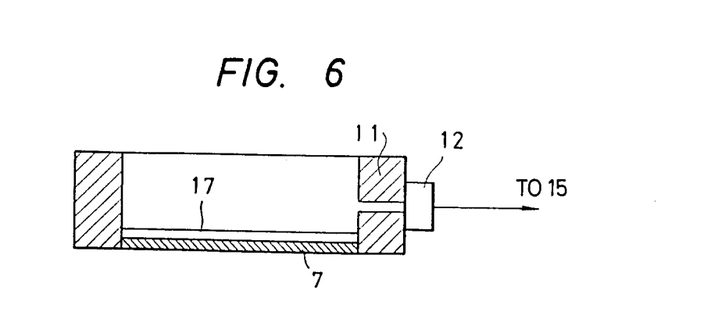

FIGS. 5 and 6 show the structures of photosensitive mediums usable in the present embodiment. In FIG. 5, the portion of the hermetically sealed microphone cell 11 which is exposed to the incident light is formed in a partition wall 17 by a substance which does not absorb light and has a sound-preventing effect, and a light absorbing substance 7 is disposed inside the partition wall. In FIG. 6, a light absorbing substance 7 is disposed on the light incidence side of a partition wall 17 formed of a substance having a thermal diffusion length $\mu$, and the partition wall 17 transmits the heat generated by the light absorbing substance 7 to thereby intermittently heat the gas in the cell. The thickness of these partition walls may preferably be the thermal diffusion length $\mu$ or less.

The thermal diffusion length $\mu$ is given by the thermal diffusivity $\alpha[cm^2/s]$ and the interruption frequency $f[Hz]$ of the substance and is operated as $$\mu = (\alpha/\pi f)^{\frac{1}{2}} [cm]$$

and therefore, if silver ($\alpha = 1.7$) is used and $f = 50$ Hz, then $\mu = 1$ [mm].

Figure 7:
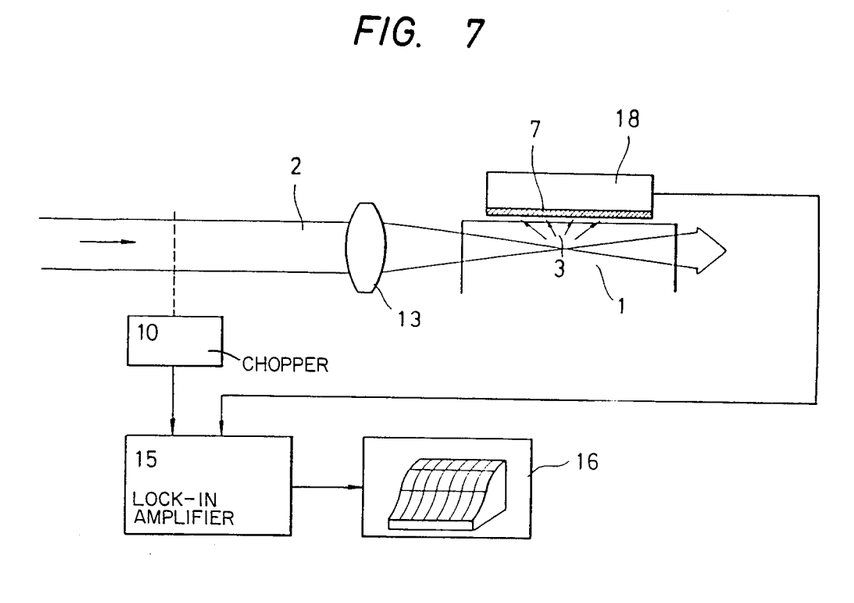

FIG. 7 shows another example of the construction of a light scattering measuring apparatus in which the present invention is embodied. In this embodiment, the energy signal is an elastic wave produced by said process D and the energy signal detecting means is piezoelectric detecting means. In FIG. 7, a conventional light source and a chopper 10 are used as light applying means which constitutes the light scattering measuring apparatus, and the photosensitive medium is formed of a light absorbing substance 7. The energy signal detecting means is a piezoelectric element 18. An applied light beam 2 interrupted by the chopper 10 is directed to an object 1 to be examined by a lens 13, and the scattered light 3 therefrom is absorbed by the light absorbing substance 7 and becomes intermittent molecular vibration, and is converted into elastic energy while being transmitted to the piezoelectric element 18, and is detected by the piezoelectric element 18. The signal from this piezoelectric element 18 is supplied to a lock-in amplifier 15 and is frequency-synchronously detected on the basis of the reference signal from the chopper 10 which interrupts the measuring beam 2, and the result is put out to a recorder 16. It is theroretically confirmed that the intensity of the thus detected piezoelectric signal is proportional to the intensity of the scattered light applied to the light absorbing substance. Accordingly, the intensity of the scattered light can be quantitatively measured.

Figure 8:
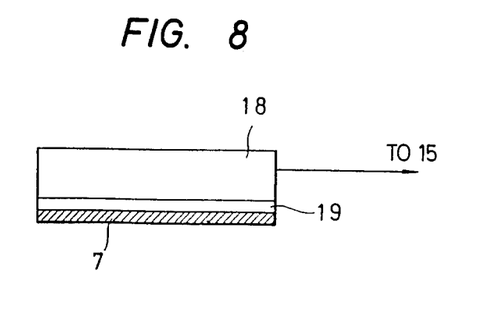

FIG. 8 shows an example of the construction of the energy signal detecting means in the present embodiment. In FIG. 8, the light absorbed by the light absorbing substance 7 becomes intermittent molecular vibration, and this is converted into elastic energy and detected by the piezoelectric element 18. In order to enable the energy to be uniformly propagated, a rear plate 19 is inserted between the light absorbing substance 7 and the piezoelectric element 18. Also, if this rear plate 19 and the light absorbing substance 7 are made integral with each other and the piezoelectric element 18 is made detachable, it will be convenient in effecting measurement by a light absorbing substance of different characteristic.

Figure 9:
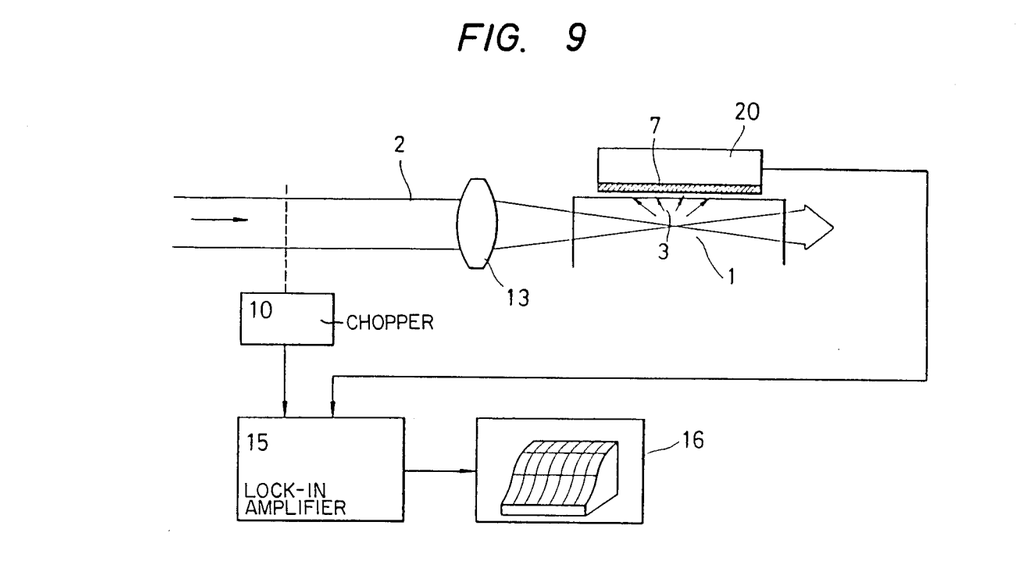

FIG. 9 shows still another example of the construction of a light scattering measuring apparatus in which the present invention is embodied. In this embodiment, the energy signal is detected by directly detecting the variation in the temperature of the surface of the light absorbing surface produced by said process B, by the use of a thermocouple. In FIG. 9, a conventional light source and a chopper 10 are used as light applying means which constitutes the light scattering measuring apparatus, the photosensitive medium is formed of a light absorbing substance 7, and energy signal detecting means 20 comprises a thermocouple. An applied light beam 2 interrupted by the chopper 10 is directed to an object 1 to be examined by a lens 13, and the scattered light therefrom is absorbed by the light absorbing substance 7 and becomes intermittent heat, and is converted into an electrical signal by the energy signal detecting means 20 comprising a thermocouple. The signal from this energy signal detecting means 20 is supplied to a lock-in amplifier 15 and is frequency-synchronously detected on the basis of the reference signal from the chopper 10 which interrupts the measuring light beam 2, and the result is put out to a recorder 16. It is theoretically confirmed that the intensity of the thus detected thermo-electrical signal is proportional to the intensity of the scattered light applied to the light absorbing substance. Accordingly, the intensity of the scattered light can be quantitatively measured.

Figure 10:
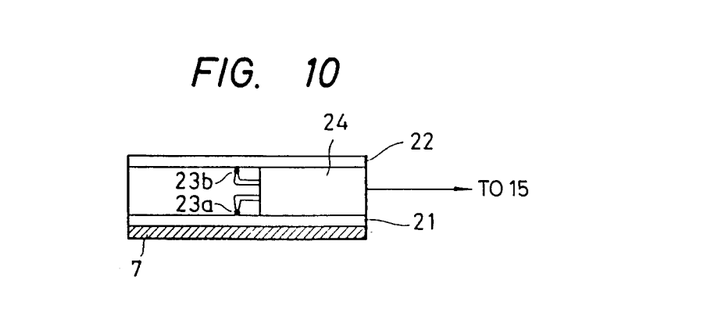
Figure 11:
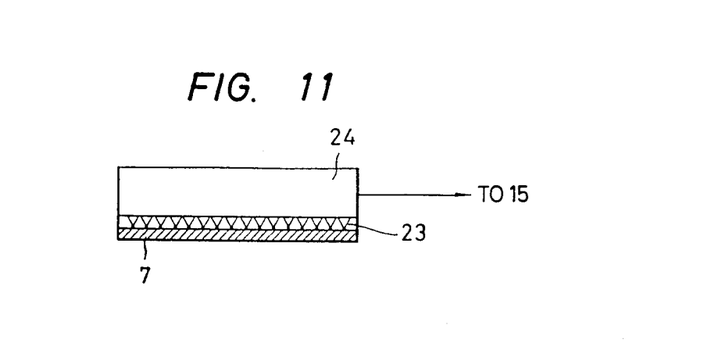

FIGS. 10 and 11 show examples of the structure of the energy signal detecting means in the present embodiment. In FIG. 10, there is shown a structure in which heat generated by the light absorbing substance 7 is detected by a thermocouple 23a through a heat conductor 21 while, on the other hand, the temperature in a heat conductor 22 for reference is detected by another thermocouple 23b and a signal indicative of the difference between the two is found by a detection signal processing portion 24 and the signal is supplied to a lock-in amplifier 15. In FIG. 11, thermocouples are arranged at predetermined locations on the light absorbing substance 7 to thereby enable the heat distributions to be measured at a time, and the intensity distribution corresponding to each angle of luminous intensity distribution of the scattered light can be found.

Figure 12:
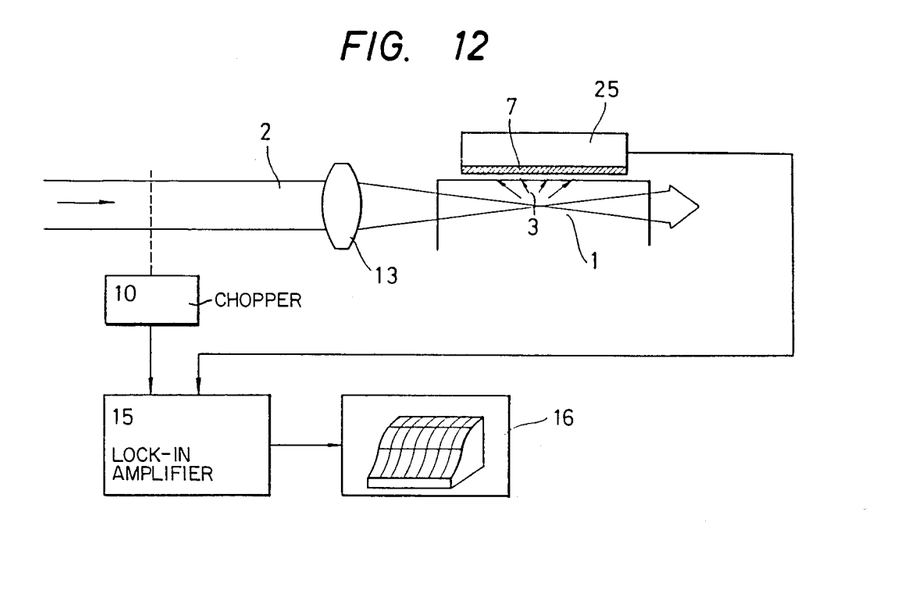

FIG. 12 shows still another example of the construction of a light scattering measuring apparatus in which the present invention is embodied. In this embodiment, the energy signal is detected by detecting as the deflection of the light beam the variation in the refractive index near the surface caused by the radiation heat wave from a light absorbing substance produced at the stage of said process B. In FIG. 12, a conventional light source and a chopper 10 are used as light applying means which constitutes the light scattering measuring apparatus, the photosensitive medium is formed of a light absorbing substance 7, and energy signal detecting means is light-heat deflection detecting means 25. An applied light beam 2 interrupted by the chopper 10 is directed to an object 1 to be examined by a lens 13, and the scattered light 3 therefrom is absorbed by the light absorbing substance 7 and becomes intermittent heat and varies the refractive index of the vicinity of the surface of the light absorbing substance, and deflects the direction of passage of the light in that area and is converted into an electrical signal by the light-heat deflection detecting means 25. The electrical signal from this light-heat deflection detecting means 25 is supplied to a lock-in amplifier 15 and is frequency-synchronously detected on the basis of the reference signal from the chopper 10 which interrupts the measuring light beam 2, and the result is put out to a recorder 16. The intensity of the thus detected light-heat deflection signal increases with an increase in the intensity of the scattered light applied to the light absorbing substance, and this relation is also theroretically confirmed. Accordingly, the intensity of the scattered light can be quantitatively measured.

Figure 13:
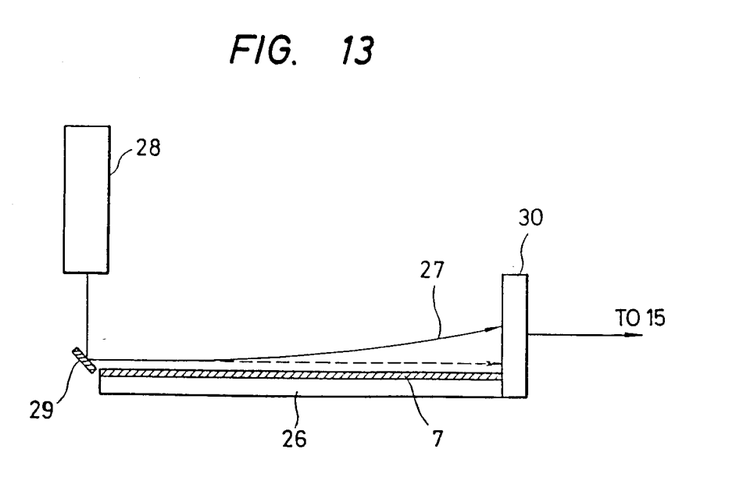

FIG. 13 shows an example of the structure of the light-heat deflection detecting means in the present embodiment. In FIG. 13, the scattered light is transmitted through a transparent flat plate 26, is absorbed by the light absorbing substance 7 present on the surface of the flat plate 26 and generates intermittent heat. The refractive index of the vicinity of the surface of the light absorbing substance is varied by this heat, and a probing light beam 27 passing through that area has its direction changed intermittently. This probing light beam 27 may preferably be a laser beam or the like which is good in directionality and small in beam diameter, and in FIG. 13, it is disposed so as to be emitted from a light source 28, be refracted by a mirror 29 and pass through the vicinity of the light absorbing substance. The positional deviation caused by the deflection of this probing light beam 27 is detected by a position sensor 30 and converted into an electrical signal thereby and supplied to the lock-in amplifier 15, whereby the intensity of the scattered light is measured.

Figure 14:
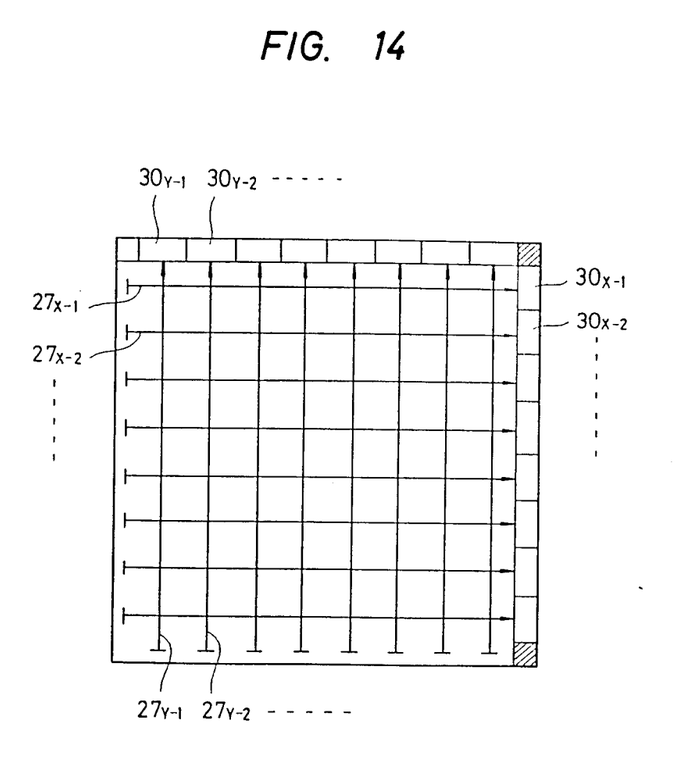
FIG. 14 shows the construction of light-heat deflection detecting means.

FIG. 14 shows another example of the structure of the light-heat deflection detecting means. In FIG. 14, the probing light beam 27 is caused to pass over the surface of the light absorbing substance 7 in the form of a matrix, and the amounts of deflection at respective positions are detected by the corresponding position sensor 30, and the temperature distribution on the surface of the light absorbing surface, i.e., the luminous intensity distribution of the scattered light, can be obtained. The probing light beam 27 may be scanned by the utilization of a pivotable mirror, or alternatively may be measured at a time by setting discrete light sources at respective corresponding positions.

By filling the area in which the light beam is deflected with a substance having a great variation in refractive index for a variation in temperature, there can be formed a heating area having a great variation in refractive index for a slight variation in temperature, and the path of travel of the light beam can be greatly changed and thus, measurement at high sensitivity can be accomplished.

Figure 15:
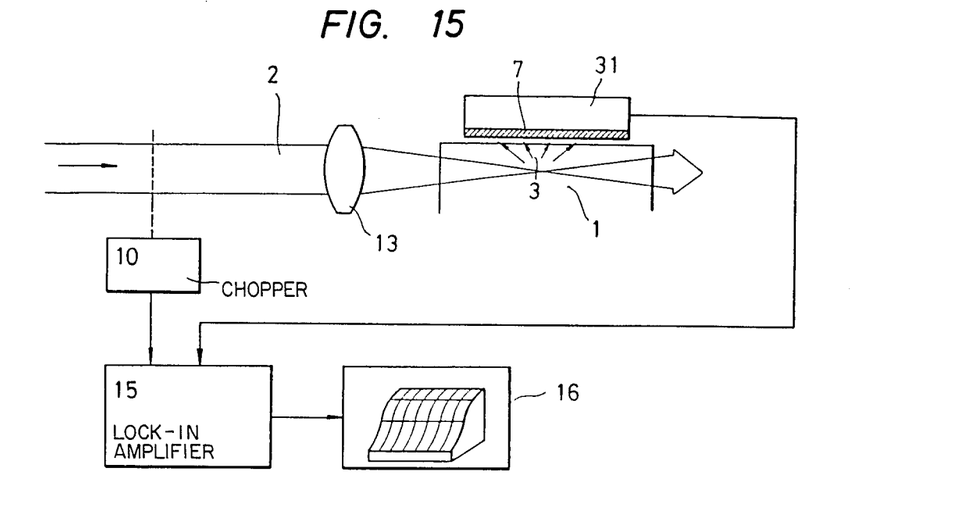

FIG. 15 shows yet still another example of the construction of a light scattering measuring apparatus in which the present invention is embodied. In this embodiment, the energy signal is detected by detecting the radiation heat wave caused by the variation in the temperature of the surface of a light absorbing surface produced at the stage of said process B, by light-heat radiation detecting means such as an infrared ray detector. In FIG. 15, a conventional light source and a chopper 10 are used as light applying means which constitutes the light scattering measuring apparatus, the photosensitive medium is formed of a light absorbing substance 7, and an infrared ray detector is used as energy signal detecting means 31. An applied light beam 2 interrupted by the chopper 10 is directed to an object 1 to be examined by a lens 13, and the scattered light 3 therefrom is absorbed by the light absorbing substance 7 and becomes intermittent radiation heat and is converted into an electrical signal by the infrared ray detector. The electrical signal from this infrared ray detector is supplied to a lock-in amplifier 15, and is frequency-synchronously detected on the basis of the reference signal from the chopper 10 which interrupts the measuring light beam 2, and the result is put out to a recorder 16. The intensity of the thus detected heat radiation signal increases with an increase in the intensity of the scattered light applied to the light absorbing substance, and this relation is also theoretically confirmed. Accordingly, the intensity of the scattered light can be quantitatively measured.

Figure 16:
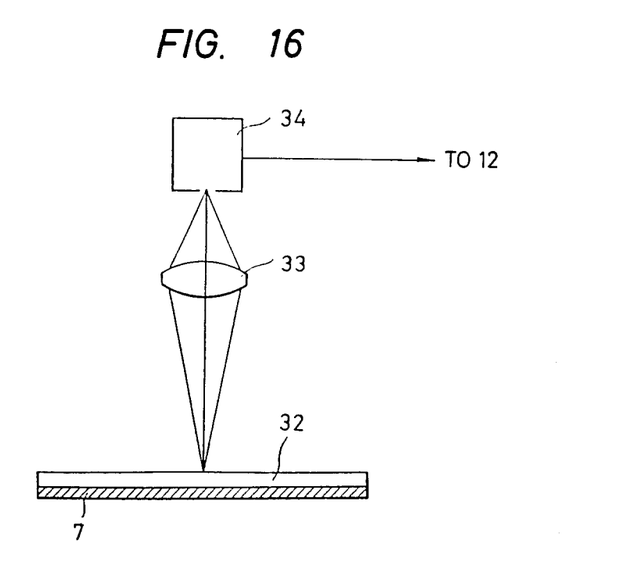

FIG. 16 shows an example of the structure of the energy signal detecting means in the above-described embodiment. In FIG. 16, the scattered light is absorbed by the light absorbing substance 7, generates intermittent heat and intermittently heats the entire rear plate 32 of good heat conductivity. From the surface of the rear plate, due to its being heated, a radiation heat wave corresponding to the then temperature changes intermittently. This is imaged on the entrance window of an infrared ray detector 34 by a lens 33 formed of a material transmitting the radiation infrared ray therethrough, and is detected by the detector 34.

Figure 17:
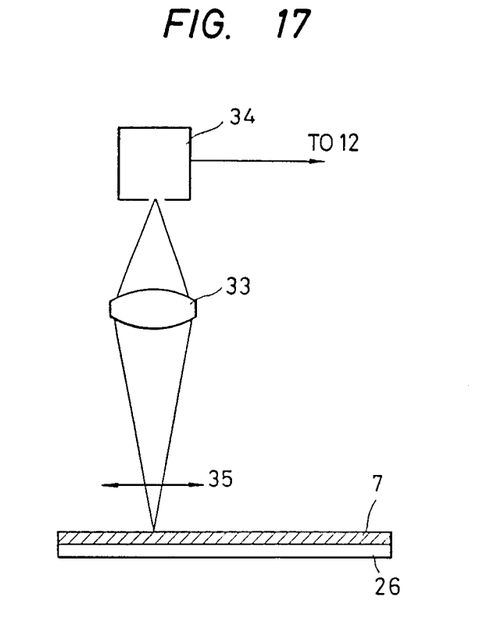

If, as shown in FIG. 17, the scattered light is transmitted through a transparent flat plate 26 and is absorbed by the light absorbing substance 7 present on the surface of the flat plate and the heat radiation radiated from the surface of the light absorbing substance is detected while a lens 33 and a detector 34 are scanned as a unit along the surface of the light absorbing substance as indicated by bilateral arrow 35, the information corresponding to the luminous intensity distribution of the scattered light can be obtained.

Figure 18:
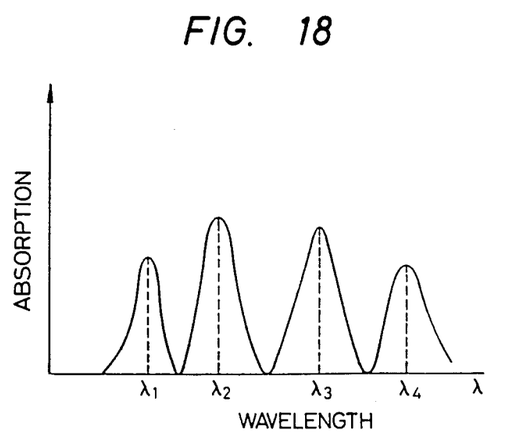
FIG. 18 is a graph showing the absorption characteristic of an absorbing substance.

FIG. 18 is a graph showing that the light absorption rates by wavelengths differ from substance to substance. If a different wavelength characteristic as shown in FIG. 18 is used as the wavelength characteristic of the light absorbing substance 7 shown in the basic construction view of FIG. 1, the intensities of scattered lights of corresponding wavelengths can be measured and thus, measurement of non-elastic scattering becomes possible.

Figure 19:
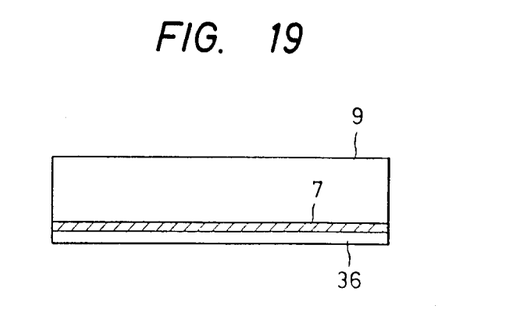

FIG. 19 shows a structure in which a filter is disposed in the path of scattered light between an object to be examined and a photosensitive medium. As shown in FIG. 19, a filter 36 is disposed on this side of the light absorbing substance 7 on which the scattered light is absorbed, and similar measurement will become possible even if the measuring wavelength range of the scattered light is controlled. If a polarizing filter is used as the filter 36, it will also become possible to obtain the polarization characteristic of the scattered light.

Figure 20:
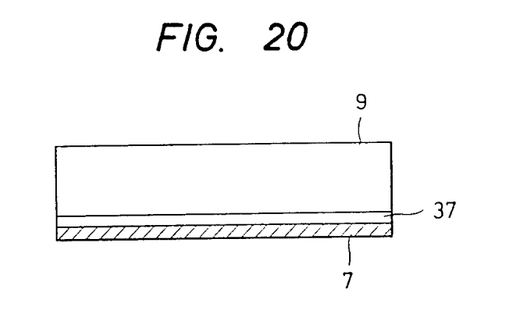

FIG. 20 shows an example in which a reflecting plate 37 is disposed on the light absorbing rear surface of the light absorbing substance 7 to thereby reduce the effective thickness of the absorbing layer to $\frac{1}{2}$, thereby enabling measurement of light scattering at high sensitivity and high accuracy.

Figure 21:
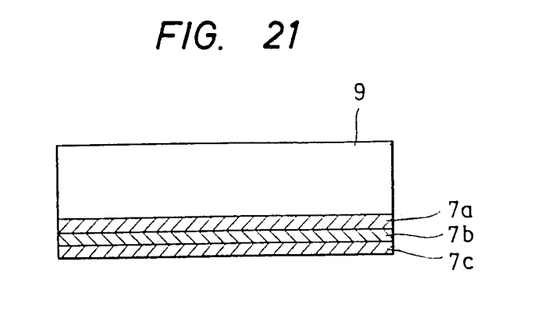

FIG. 21 shows an example in which the light absorbing substance is made into a multilayer structure and substances 7a–7c of different spectral absorption characteristics are disposed in the respective layers. By such disposition, it becomes possible to measure signals of various wavelengths at a time. That is, in the respective layers, light energy having a different wavelength characteristic is converted into molecular vibrational energy which is transmitted to the energy signal detecting means, but at that time, there occurs a phase delay corresponding to the distance from each layer to the energy signal detecting means. So, when the signal of the scattered light is to be obtained by frequency-synchronous detection, if the detection is effected for each corresponding phase shift, the signals from the respective layers can be separated from one another.

Figure 22:
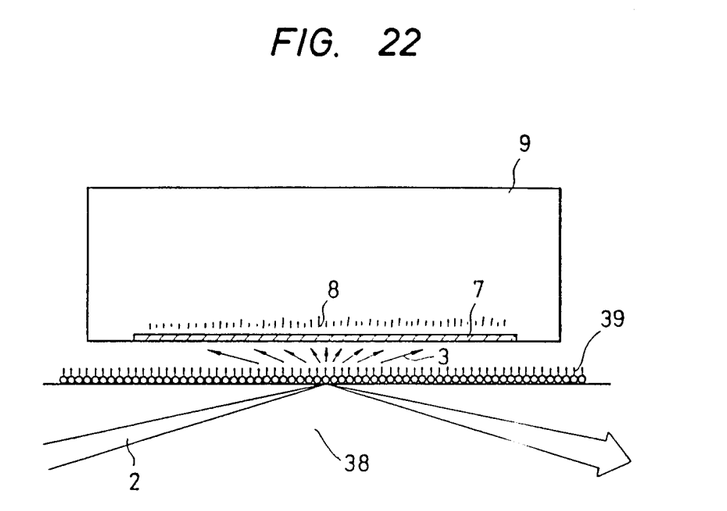

FIG. 22 shows an embodiment in which the present invention is applied to the light scattering by a monomolecular film on the surface of liquid. In FIG. 22, an applied light 2 is caused to enter at such an angle that it enters from below the surface of liquid and is totally reflected by the interface of liquid. On the totally reflecting interface, the light energy is transmitted as an evanescent wave to the monomolecular film 39 on the surface of liquid and the light absorbing substance, whereby scattered light 3 is created. The light scattering characteristic by the monomolecular film 39 and the light absorbing substance can be detected by detecting the scattered light on the basis of each said method by energy signal detecting means 9 disposed on the surface of liquid.

Figure 23:
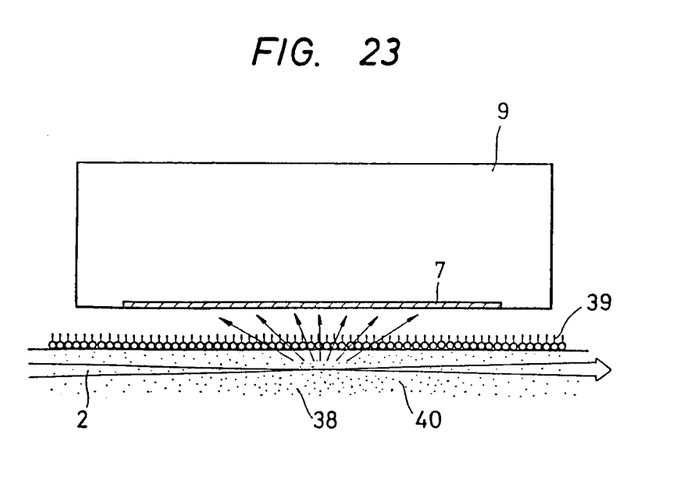

FIG. 23 shows an embodiment for evaluating the light scattering characteristic below the surface of liquid in an LB (Langmuir-Blodgett) film forming apparatus. The state of monomolecular developing liquid can be detected by measuring the scattered light by a scattering factor 40 in liquid, and control of film formation also becomes possible on the basis of this information.

The information in each portion can be patternized by stopping down the diameter of the applied light beam as required, eliminating the mutual influence between the scattered lights in the object to be examined and causing the applied light beam to scan along a predetermined plane in the object to be examined. By processing the thus obtained electrical signal and scanning signal by a computer and displaying the same by a display device, microscopic information can be patternized and grasped.

According to the present invention, as described above, light scattering such as elastic scattering and non-elastic scattering, including a light scattering component of a great angle of scattering which it has heretofore been difficult to measure, can be measured at high sensitivity and high accuracy. Therefore, not only the fluctuation of the refractive index in the object to be examined and the presence of fine particles therein can be detected, but also molecular structural information can be obtained and also, the present invention can be applied to a Langmuir-Blodgett film forming apparatus and greatly contributes to the analysis of properties of matters.

We claim:

1. A scattered light measuring apparatus, usable to measure the light scattering properties of an object to be examined, said apparatus comprising:
    light applying means for applying intermittent light to the object to be examined,
    a photosensitive medium having an absorbing layer on a detector disposed along and out of contact with the surface of the object to be examined, said absorbing layer being capable of absorbing scattered light intermittently emitted from the surface of the object to be examined depending on the physical properties of the object when exposed to said intermittent light and converting the absorbed scattered light into a molecular vibrational energy signal,
    energy signal detecting means for detecting the energy signal produced in said photosensitive medium, and
    molecular vibration measuring means for measuring the molecular vibrational energy by synchronizing the detected energy signal with a reference frequency signal from said light applying means.

2. A scattered light measuring apparatus according to claim 1, wherein said light applying means comprises a light source and a chopper.

3. A scattered light measuring apparatus according to claim 1, wherein the energy signal is a sound wave, and said energy signal detecting means includes opto-acoustic detecting means.

4. A scattered light measuring apparatus according to claim 3, wherein said opto-acoustic detecting means includes a microphone cell.

5. A scattered light measuring apparatus according to claim 1, wherein the energy signal is a conducted heat wave, and said energy signal detecting means includes heat detecting means.

6. A scattered light measuring apparatus according to claim 5, wherein said heat detecting means includes a thermocouple.

7. A scattered light measuring apparatus according to claim 1, wherein the energy signal is a radiation heat wave, and said energy signal detecting means includes photothermal detecting means for detecting optical deflection caused by the radiation heat wave.

8. A scattered light measuring apparatus according to claim 1, wherein the energy signal is a radiation heat wave, and said energy signal detecting means includes photothermal radiation detecting means.

9. A scattered light measuring apparatus according to claim 8, wherein said photothermal radiation detecting means includes an infrared ray detector.

10. A scattered light measuring apparatus according to claim 1, wherein one or more light absorbing substances having different spectral absorption characteristics are superposed as said photosensitive medium.

11. A scattered light measuring apparatus according to claim 1, wherein a filter is interposed between the object to be examined and said photosensitive medium.

12. A scattered light measuring apparatus according to claim 11, wherein said filter includes a polarizing filter.

13. A scattered light measuring apparatus according to claim 1, wherein a reflecting object is provided on a light absorbing rear surface of said photosensitive medium.

14. A scattered light measuring apparatus according to claim 1, wherein said photosensitive medium is of a multilayer structure, said energy signal detecting means includes means for detecting the phases of energy signals corresponding to the respective layers, and said molecular vibration measuring means includes means for substantially simultaneously measuring the different spectral characteristics of scattered lights from the phase shifts of said energy signals.

15. A scattered light measuring apparatus, usable to measure the light scattering properties of an object to be examined, said apparatus comprising:
    light applying means for applying intermittent light to the object to be examined,
    a photothermal converting medium having an absorbing layer on a detector disposed along and out of contact with the surface of the object to be examined, said absorbing layer being capable of absorbing scattered light intermittently emitted from the surface of the object to be examined depending on the physical properties of the object when exposed to said intermittent light and converting the absorbed scattered light into heat energy,
    elastic wave detecting means cooperating with said detector for detecting an elastic wave created by the heat energy as an electrical signal through piezoelectric conversion, and
    heat variation measuring means for measuring the amount of said heat energy from the electrical signal.

16. A scattered light measuring apparatus according to claim 15, wherein said elastic wave detecting means includes a piezoelectric element.

17. A scattered light measuring apparatus according to claim 15, wherein said light applying means comprises a light source and a chopper.

* * * * *

UNITED STATES PATENT AND TRADEMARK OFFICE
CERTIFICATE OF CORRECTION

PATENT NO. : 4,682,897

DATED : July 28, 1987

INVENTOR(S) : KENJI SAITO, ET AL.

It is certified that error appears in the above-identified patent and that said Letters Patent is hereby corrected as shown below: Title page:

<u>AT [56] UNDER REFERENCES CITED/OTHER PUBLICATIONS</u>

Line 2, "Their" should read --Thin--.

<u>COLUMN 2</u>

Line 23, "accordihg" should read --according--.

Signed and Sealed this

First Day of December, 1987

Attest:

DONALD J. QUIGG

*Attesting Officer*  *Commissioner of Patents and Trademarks*